US010933193B2

(12) United States Patent
Boström et al.

(10) Patent No.: US 10,933,193 B2
(45) Date of Patent: *Mar. 2, 2021

(54) INJECTION DEVICE

(71) Applicant: SHL GROUP AB, Nacka Strand (SE)

(72) Inventors: Anders Boström, Solna (SE); Elin Gabrielsson, Hässelby (SE)

(73) Assignee: SHL MEDICAL AG, Zug (CH)

(*) Notice: Subject to any disclaimer, the term of this patent is extended or adjusted under 35 U.S.C. 154(b) by 884 days.

This patent is subject to a terminal disclaimer.

(21) Appl. No.: 15/461,220

(22) Filed: Mar. 16, 2017

(65) Prior Publication Data

US 2017/0182250 A1 Jun. 29, 2017

Related U.S. Application Data

(63) Continuation of application No. 14/241,627, filed as application No. PCT/SE2012/050908 on Aug. 28, 2012, now Pat. No. 9,656,025.

(Continued)

(30) Foreign Application Priority Data

Aug. 31, 2011 (SE) .................................... 1150788-6

(51) Int. Cl.
*A61M 5/20* (2006.01)
*A61M 5/315* (2006.01)
*A61M 5/32* (2006.01)

(52) U.S. Cl.
CPC ...... *A61M 5/2033* (2013.01); *A61M 5/31515* (2013.01); *A61M 5/3204* (2013.01);
(Continued)

(58) Field of Classification Search
CPC ...... A61M 5/2033; A61M 5/326; A61M 5/20; A61M 2005/3267; A61M 2005/3268;
(Continued)

(56) References Cited

U.S. PATENT DOCUMENTS

| 4,642,099 A | 2/1987 | Phillips et al. |
| 5,658,259 A * | 8/1997 | Pearson ............. A61M 5/2033 |
| | | 604/136 |

(Continued)

FOREIGN PATENT DOCUMENTS

WO 2011/032731 3/2011

OTHER PUBLICATIONS

Sweden Patent Office, Int'l Search Report in PCT/SE2012/050908, dated Dec. 11, 2012.

(Continued)

*Primary Examiner* — Manuel A Mendez
*Assistant Examiner* — Justin L Zamory
(74) *Attorney, Agent, or Firm* — McDonnell Boehnen Hulbert & berghoff LLP

(57) ABSTRACT

An injection device is presented having a housing, a container holder, a first and a second energy accumulating member arranged in the interior of the housing adapted to accumulate and store energy, a sleeve, a plunger holder operationally associated with said first energy accumulating member such that the plunger holder and the container holder are axially moveable in relation to the housing a predetermined distance towards the proximal end of the injection device from an initial position to a position following needle penetration, and a plunger rod being operationally associated with said second energy accumulating member such that the plunger rod is axially moveable in relation to the container holder, wherein in the initial position movement of the plunger holder is substantially inhibited by at least one first biasable member that recoils when being overlapped by an opening and/or recess of the sleeve such that the plunger holder is released.

18 Claims, 10 Drawing Sheets

Related U.S. Application Data

(60) Provisional application No. 61/529,325, filed on Aug. 31, 2011.

(52) U.S. Cl.
CPC ............... *A61M 2005/206* (2013.01); *A61M 2005/2013* (2013.01); *A61M 2005/2086* (2013.01)

(58) Field of Classification Search
CPC .... A61M 2005/208; A61M 2005/2013; A61M 2005/206; A61M 2005/3247; A61M 2005/3264
See application file for complete search history.

(56) References Cited

U.S. PATENT DOCUMENTS

| | | |
|---|---|---|
| 7,361,160 B2 | 4/2008 | Hommann et al. |
| 2005/0101919 A1 | 5/2005 | Brunnberg |
| 2006/0224124 A1 | 10/2006 | Scherer |
| 2010/0137798 A1 | 6/2010 | Streit et al. |
| 2010/0137801 A1 | 6/2010 | Streit et al. |
| 2010/0191217 A1 | 7/2010 | Hommann et al. |
| 2010/0249705 A1* | 9/2010 | Kronestedt ......... A61M 5/2033 604/134 |

OTHER PUBLICATIONS

Sweden Patent Office, Written Opinion in PCT/SE2012/050908, Dec. 11, 2012.

* cited by examiner

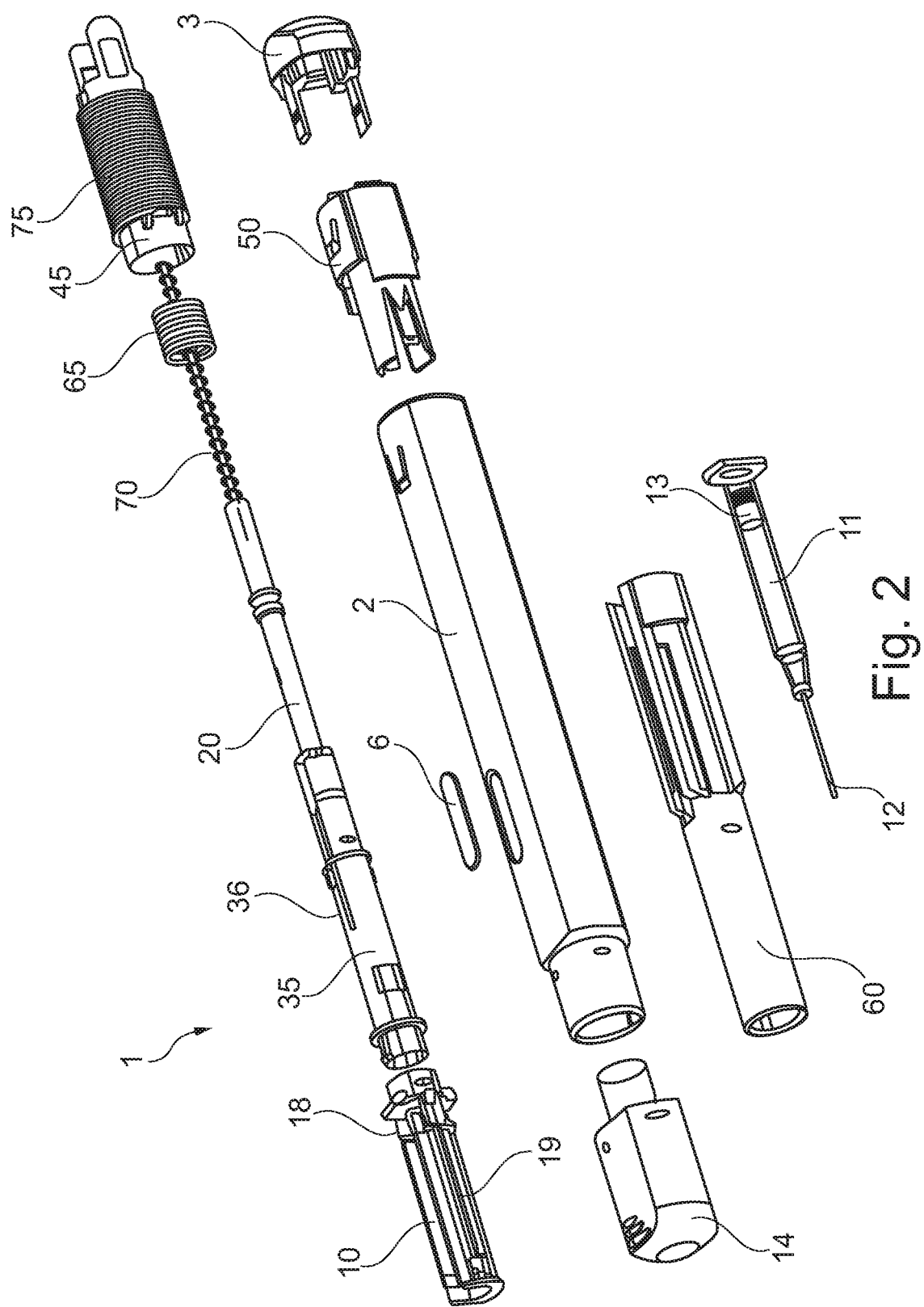

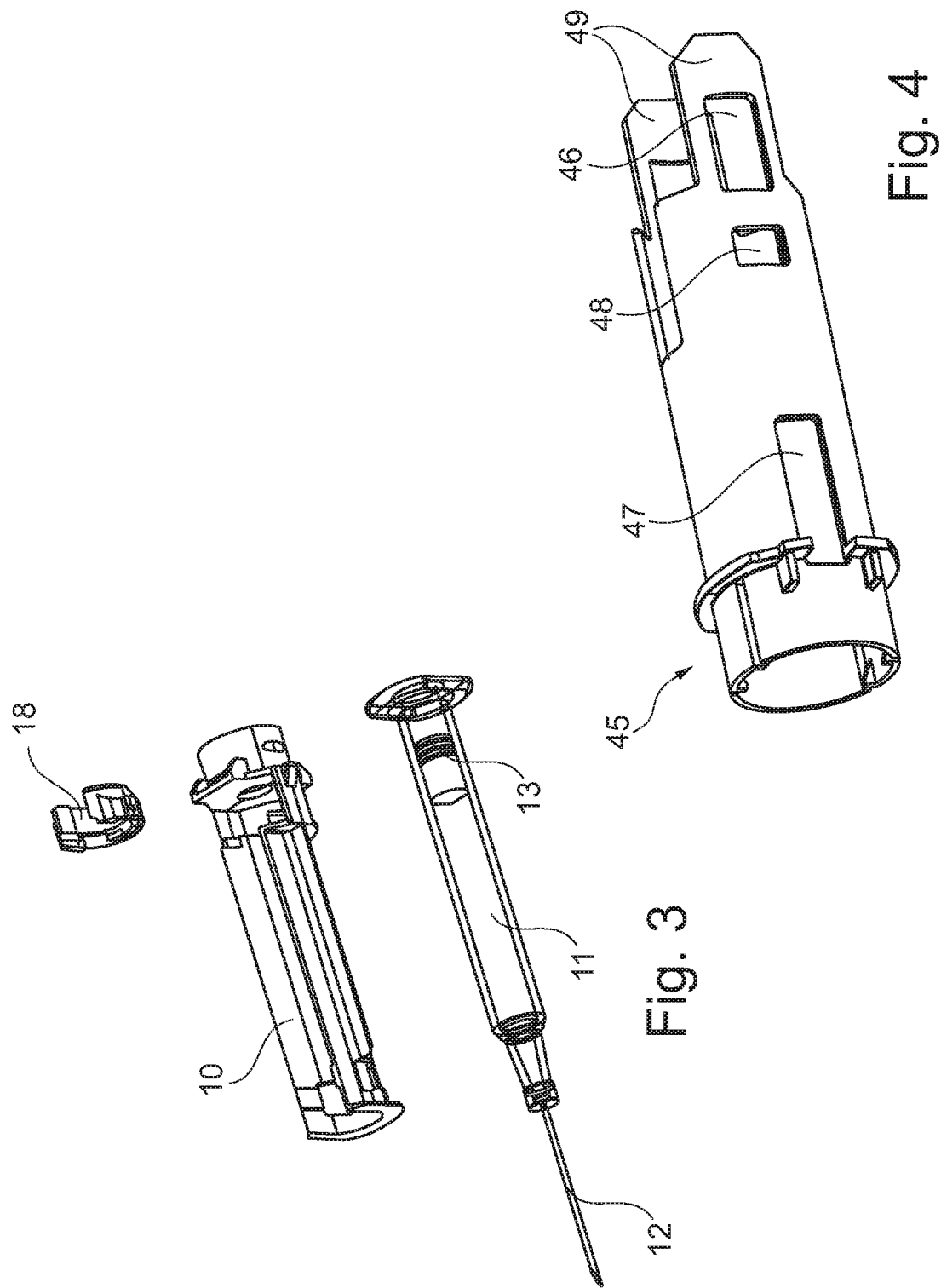

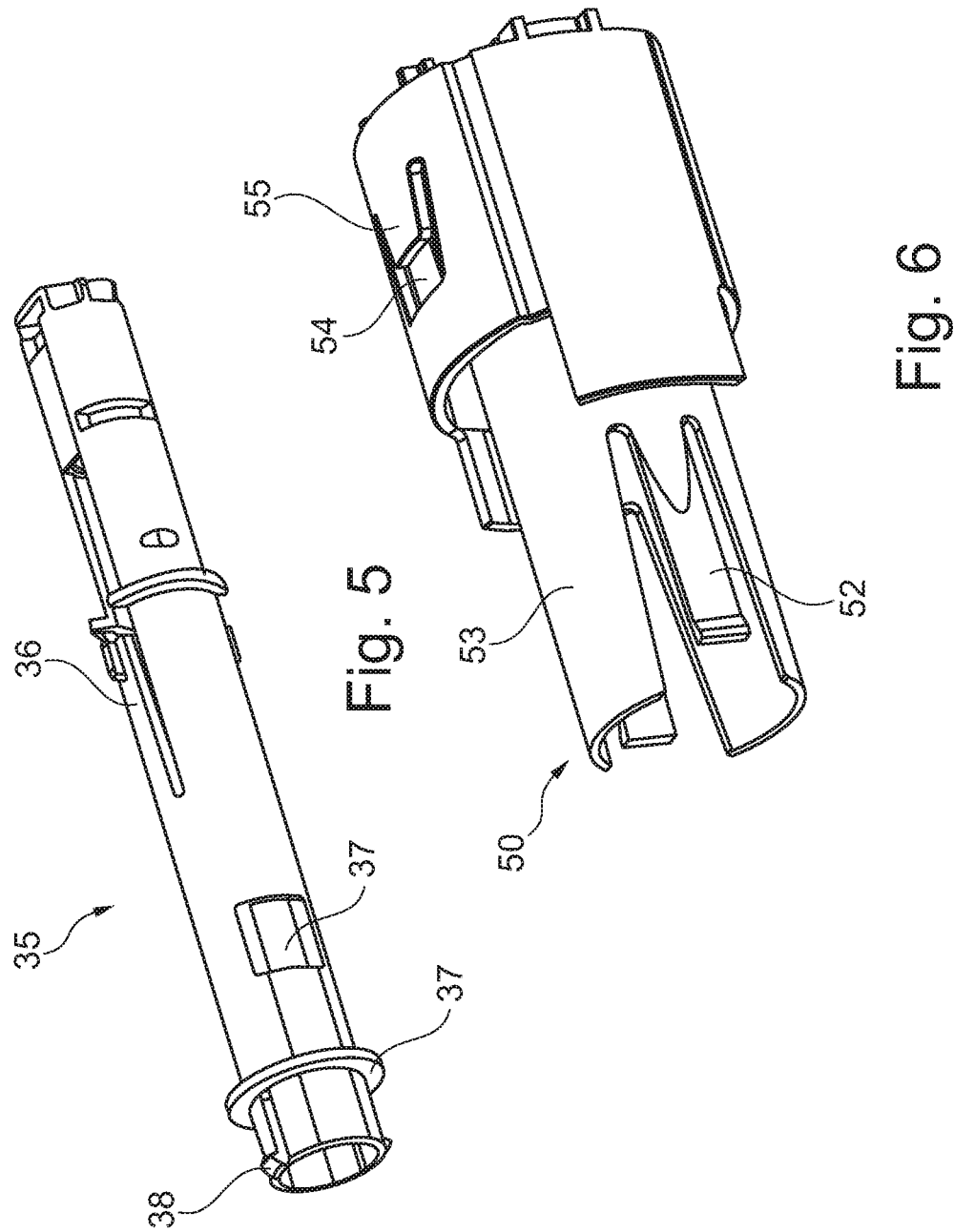

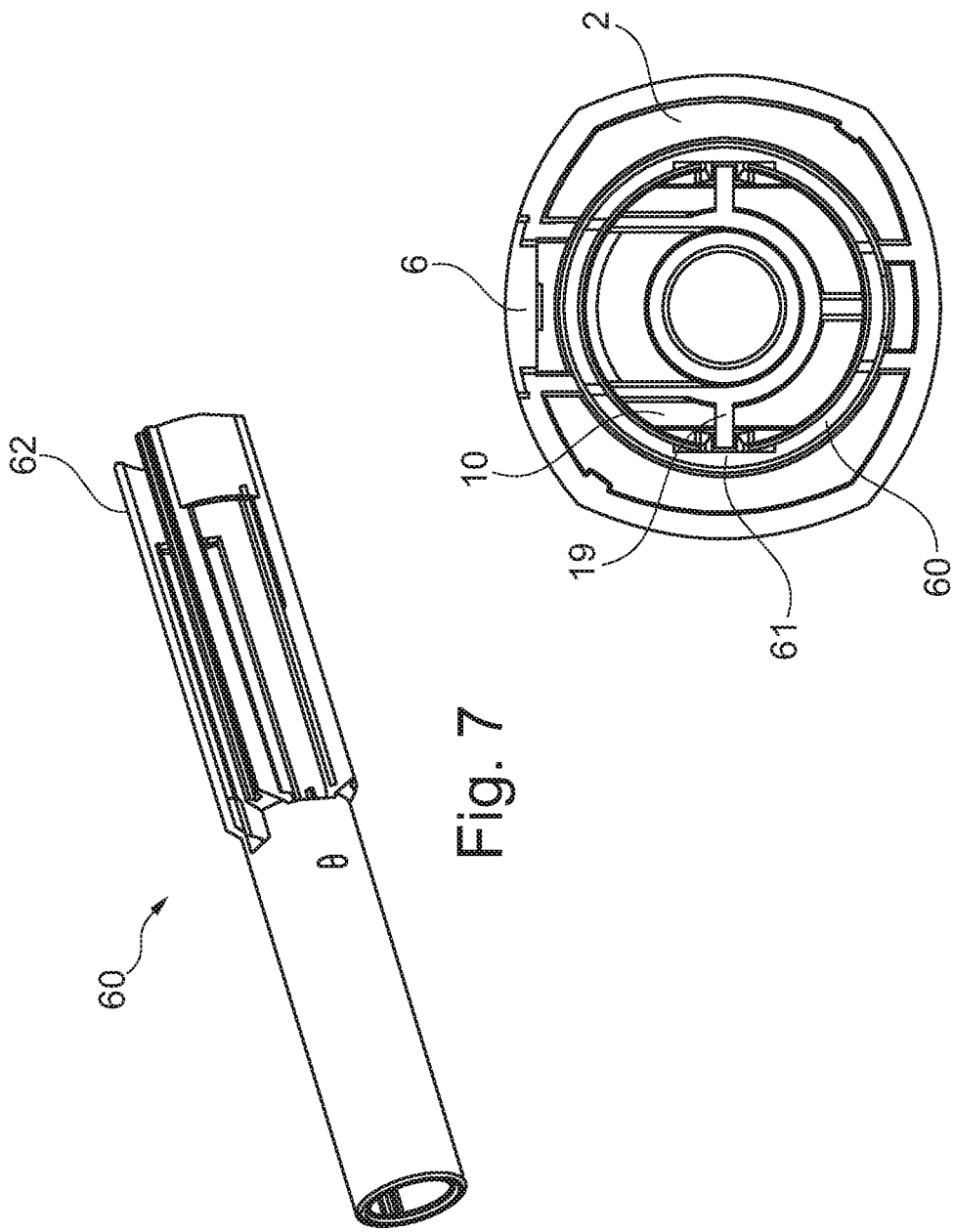

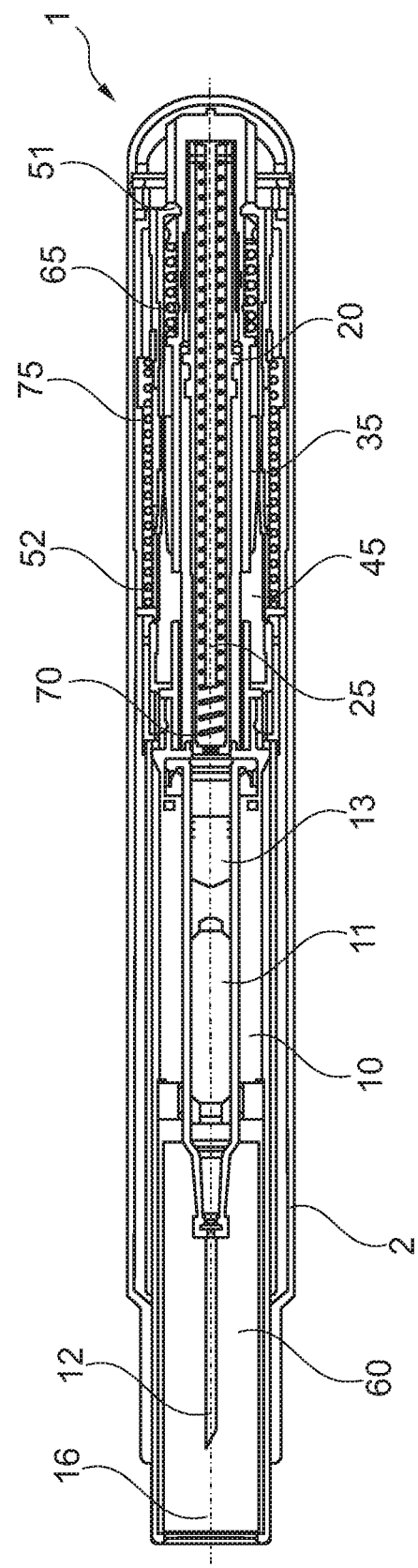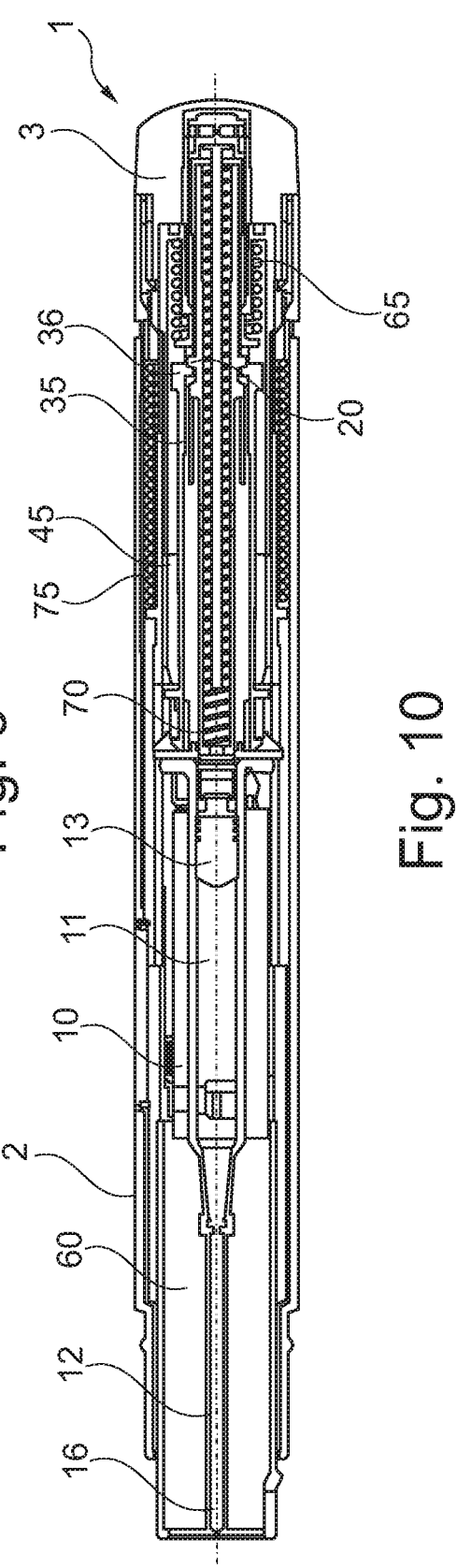

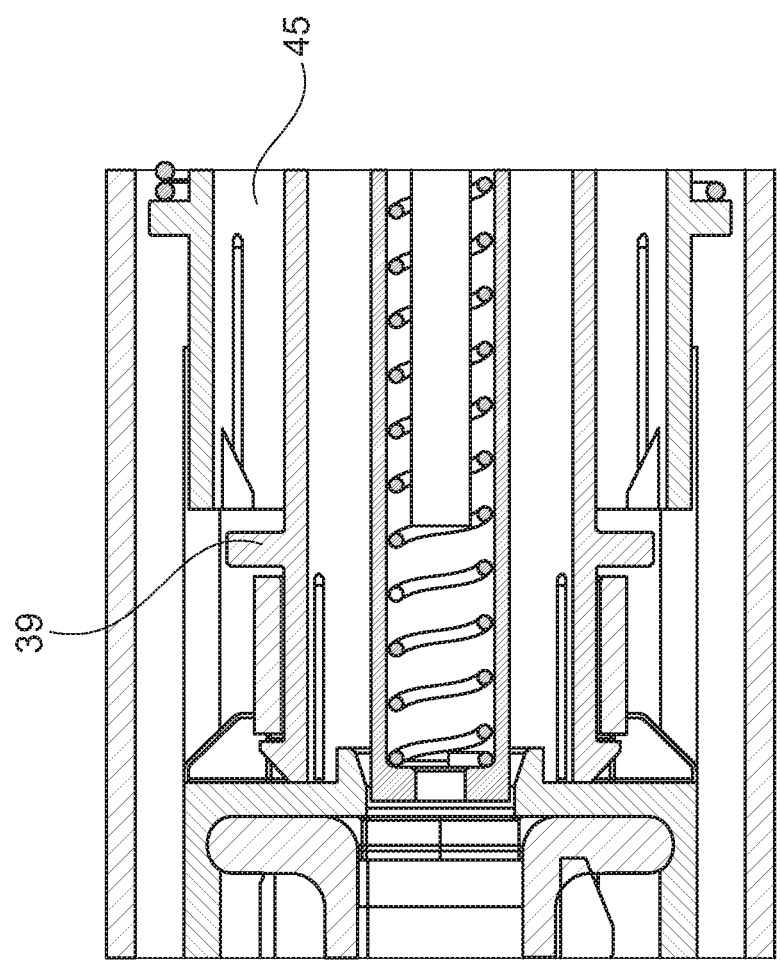

INJECTION DEVICE

CROSS REFERENCE TO RELATED APPLICATIONS

The present application is a continuation of U.S. patent application Ser. No. 14/241,627 filed May 12, 2014, now U.S. Pat. No. 9,656,025, which is a U.S. National Phase Application pursuant to 35 U.S.C. § 371 of International Application No. PCT/SE2012/050908 filed Aug. 28, 2012 which claims priority to U.S. Provisional Patent Application No. 61/529,325 filed Aug. 31, 2011 and Swedish Patent Application No. 1150788-6, filed Aug. 31, 2011. The entire disclosure contents of these applications are herewith incorporated by reference into the present application.

TECHNICAL FIELD

The present disclosure relates to an injection device having several automatic functions such as automatic penetration, automatic injection and automatic safety means for preventing from accidental needle sticks and in particular to a disposable, single use injection device having a mechanism that provides all these functions in a reliable and space-saving manner and that may be used for auto-injection.

BACKGROUND

The present disclosure relates to injection devices for injecting medicaments or medicinal substances, such as insulin or hormones, in fluid form through a needle.

Auto-injectors, or pen-injectors have been on the market for many years. One of the first auto-injectors was developed for war-times and was activated by pressing the injector against a body part. The main concern was to have the medicament injected as fast as possible without much concern for the patient or for handling safety aspects. During the recent years some medicaments have been developed that have to be injected by the patients themselves. Therefore, depending on the intended use and type of medicament, injection devices having a varying degree of automatic functions have been developed to facilitate injection of medicaments in a reliable and safe manner for patients and even for trained personnel; e.g. physicians, nurses.

Auto-injector devices having a penetration function often comprise a housing, a container holder carrying a medicament container with a needle and a plunger rod as well as a spirally wound compression spring. When the devices are actuated, the container holder and the plunger rod, which are slidable in the housing, are jointly driven towards the patient's skin by the force of a compression spring. Thereby, penetration of the needle is effected. Normally, the devices are actuated by the user pressing a movable button. Actuation of the movable button may be inhibited until the device is positioned at a delivery site and a movable needle cover, which protrudes from the housing, is pushed against a patient's skin. However, many patients and practitioners prefer penetration to be automatic once the device is positioned at the delivery site.

Auto-injection devices further having an automatic injection function often comprise an additional spirally wound compression spring acting on the plunger rod which in turn acts on a stopper inside a medicament container for expelling a medicament through the needle. The medicament is often injected following penetration once the container holder and the plunger rod are jointly moved to a predetermined position.

Some auto-injector devices may have an automatic safety function for preventing from accidental needle sticks by covering the needle with a needle cover when the device is withdrawn from the patient's skin.

Normally, auto-injection devices either do not provide all desired automatic functions and/or require several mechanisms with multiple individual movable parts, including small members and parts with complex shapes, in order to do so. However, this may lead to devices which do not provide all the functions desired by the patients and, moreover, devices which are larger and comprise more components than necessary and difficult to manufacture and assemble.

U.S. Pat. No. 7,361,160 discloses an injection device including a receptacle for an active substance, which is connected to an injection needle and is accommodated inside a sliding sleeve that can be displaced within a housing by means of a driving force. A sleeve-shaped needle-protecting device is displacable within the housing by means of a spring such that said needle-protecting device moves forward and extends past the injection needle in an axial direction when the injection needle is withdrawn from the body tissue. A lock prevents the needle-protecting device from being manually pushed backward. The device can be activated when a sliding sleeve is back in its retracted position. However, the device does not automatically perform penetration when positioned at the delivery site and also is difficult to manufacture and assemble given that several independent movable and non-movable part are required for providing the penetration, injection and safety functions.

US 2006/0224124 discloses a device for administering an injectable product including a drive unit for driving a drive member in an administering direction, a release mechanism for releasing the drive unit and a locking mechanism which, when locked, prevents the release mechanism from being operated. The locking mechanism is displaceable along the longitudinal axis of the device from a locked to an unlocked position and the release mechanism can be moved radially with respect to the longitudinal axis for releasing purposes when the locking mechanism is in the unlocked position. However, also this device does not provide automatic penetration when positioned at a delivery site. Furthermore, several individual parts are required in order to provide the above-mentioned functions.

U.S. Pat. No. 4,642,099 discloses a rumen injector having a body, an interacting piston and a cylinder mounted within the body and a needle fixed to the cylinder. The cylinder is movable from a rest position to a cocked position and the piston is movable within the cylinder from a rest position to a cocked position so that in use of the injector the cylinder is first released to cause insertion of the needle and then the piston is released to cause injection of a dose into the rumen of the animal. While the cylinder is released when a shield mounted on the forward end of the body is pressed against the animals skin, the device does, inter alfa, not provide the required safety functions for preventing accidental needle sticks after the device is used.

SUMMARY

In order to overcome one or several of the above-mentioned problems, an injection device according to independent claim 1 is provided.

Further aspects, improvements and variations are disclosed in the dependent claims, the figures and the description.

In the present application, when the term "distal" is used, this refers to the direction pointing away from the dose delivery site. When the term "distal part/end" is used, this refers to the part/end of the delivery device, or the parts/ends of the members thereof, which is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which is/are located closest to the dose delivery site.

The injection device of the present disclosure comprises a housing and a container holder arranged within the housing. The container holder is configured for accommodating a medicament container. The medicament container may be a commonly used medicament container having a needle attached to one end thereof and a stopper sealingly and slidable arranged inside said medicament container at the other end thereof. However, according to embodiments of the present disclosure, the needle can also be attached to the medicament container holder and be fluidly connectable to a medicament container inserted into said holder.

The person skilled in the art will notice that the medicament container is an optional component of the injection device in that it may be insertable into the injection device by the user, for example by replacing an empty medicament container after use of the injection device. Moreover, the injection device is not necessarily delivered in its fully assembled state, i.e. with the medicament container already accommodated in the injection device upon delivery of the injection device.

The container holder may comprise one or more structures for holding the medicament container. For example, the container holder may comprise a flexible collar that is biased outwardly when the container is inserted and snaps back subsequently, surrounding and holding the container.

Initially, the medicament container preferably contains a defined dose of a substance to be injected, such as a medicament, insulin or hormones. Initially, the stopper preferably is arranged at the distal end of the medicament container.

The housing may comprises an outer body, a rear cap and a window. In the assembled state of the injection device, the rear cap may close a distal opening of the outer body. The outer body and the rear cap may form the outer surface or appearance of the injection device. However, the present disclosure also encompasses configurations where the housing comprises less or additional housing parts.

The housing parts may have a generally cylindrical configuration or have the general shape of a prism and may have a circular, elliptical, square, or substantially square cross section perpendicular to the longitudinal axis of the device. A removable front cap may close the proximal opening of the housing.

In a preferred embodiment, the rear cap is coaxially connected to the outer body. The outer surface of the rear cap may be provided with mating engagement structures that provide a shape fit towards the outer body. However, the rear cap and the outer body may also be snap-fitted to each other. The connection may be releasable or not.

The window may be a transparent or semi-transparent element inserted into or covering an opening of the outer body.

The injection device of the present disclosure further comprises at least one sleeve which is slidably arranged in the housing and a plunger holder which is arranged for being connectable to the container holder, e.g., by a snap connection with hooks provided on the plunger holder and/or on the container holder. The plunger holder is operationally associated with at least one first energy accumulating member, such that, due to an output axial force from said first energy accumulating member, the plunger holder and the container holder are axially moveable in relation to the housing a predetermined distance towards the proximal end of the injection device. The first energy accumulating member may be partially arranged around the plunger holder.

The plunger holder may have the general shape of a hollow cylinder. Furthermore, the plunger holder may comprise openings and/or circumferentially extending ribs and/or other stop structures, the functionality of which will be detailed further below.

Preferably, when the injection device of the present disclosure is in an initial position, the first energy accumulating member is biased and pushes the plunger holder towards the proximal end of the device. However, movement of the plunger holder is inhibited such that the plunger holder and the container holder are axially moved when the container holder is released. In this position, movement of the plunger holder towards the proximal end of the device is substantially inhibited by at least one first biasable member interacting with the plunger holder. Preferably, the first biasable member is overlapped by the sleeve and, thus, unable to deflect and/or to recoil until being overlapped by a first opening and/or a first recesses provided in said sleeve.

The initial position may be the position in which the device is delivered to the patient after taking off the removable the cap. In the initial position, the container holder preferably is located within the outer body. More preferably, the container holder is located within the outer body such that the needle is covered by and/or retracted into the outer body. According to embodiments of the present disclosure needle penetration may be effected by moving the plunger holder and the container holder in the proximal direction from the initial position to a position following needle penetration when the plunger holder is released.

The outer body may have a stepped configuration to stop the container holder at the final penetration depth. However, alternatively, the outer body may not have a stepped configuration but rather the same cross sectional size and shape at its proximal end distal ends. In such case, said stops, if required, may be provided by other parts, such as additional housing parts or stop ribs.

Furthermore, the outer body may comprise ribs and/or recesses to guide movement of the sleeve and/or a needle cover operationally associated with said sleeve. The sleeve and/or the needle cover, in turn, may comprise ribs and/or recesses to guide movement of the container holder.

The at least one first biasable member may comprise at least one biasable lever, preferably a biasable lever with a hook. In embodiments, the injection device of the present disclosure comprises an inner body that is substantially fixedly arranged in relation to the housing. The at least one first biased member may be formed integrally with said inner body and, more preferably, is formed integrally with a tubular portion of the inner body which is at least partially disposed between the plunger holder and the sleeve. The inner body may be releasably connected to the outer body, preferably snap fitted to the outer body.

According to embodiments of the disclosure the surface of the at least one first biasable member and/or the surface of the plunger holder which interact in order to inhibit movement of the plunger holder in the proximal direction when the plunger holder is in the initial position is tapered and/or angled such that, when the biasable member is able to recoil because it is overlapped by the first opening and/or the first recess of the sleeve, the biasable member is deflected by the plunger holder being pushed in the proximal direction by the output axial force from the first energy accumulating member. Preferably, the at least one first biasable member is deflected in a radially outward direction, i.e., away from the longitudinal axis of the injection device. Alternatively, the biasable member may be biased when assembling the device and recoil autonomously when overlapped by the opening or recess of the sleeve such that tapered surfaces are not required.

The injection device of the present disclosure further comprises a plunger rod that is arranged such that a proximal end thereof can contact the stopper of the medicament container. The plunger rod is slidable with respect to the plunger holder and slidable with respect to the container holder. Furthermore, the plunger rod is operationally associated with a second energy accumulating member, such that, due to an output axial force from said second energy accumulating member, the plunger rod is axially movable in relation to the container holder towards the proximal end of the injection device. The plunger holder may be arranged around the plunger rod and/or the plunger rod may be arranged around the second energy accumulating member.

In the initial position of the injection device, the plunger rod preferably is in a locked position. In said locked position movement of the plunger rod relative to the container holder towards the proximal end of the injection device preferably is substantially inhibited by at least one biasable member of the plunger holder, i.e., a second biasable member, interacting with the plunger rod. The second biasable member may be configured to recoil and/or to be deflected when the plunger holder reaches the final penetration depth such that the plunger rod is released and moved towards the proximal end of the injection device by the output axial force from said second energy accumulating member, moving from a locked position to a position after medicament injection and thereby injecting the medicament contained in the medicament container.

In an embodiment, the container holder may be configured to guide the plunger rod into the medicament container and/or during medicament injection. Additionally or alternatively, the container holder may also be configured to stop the plunger rod when the correct dose has been delivered. The container holder may be provided with appropriate structures or stops for any of the above purposes. Furthermore, the container holder may comprise a flange that interacts with the steps or stop structures of the outer body to restrict movement of the container holder when the final penetration depth is reached.

Preferably, recoiling and/or deflection of the at least one second biasable member is inhibited until the plunger holder reaches the final penetration depth by the inner body abutting the biasable member. For example, the at least one second biasable member may abut against the tubular portion of the inner body. More preferably, when the plunger holder moves towards the proximal end of the injection device and reaches the final penetration depth, the at least one second biasable member moves past the proximal end of the tubular portion of the inner body and, therefore, is able to recoil and/or can be deflected. However, recoiling and/or deflection of the at least one second biasable member may also be inhibited by other components of the device, e.g., the sleeve or the outer body. Furthermore, the at least one second biasable member may not have to move past the proximal end of any such component but can also recoil and/or deflect when reaching an opening or recess provided in the respective component.

The second biasable member may interact with a slot provided in the plunger rod. In particular, the at least one second biasable member may comprise at least one biasable lever, preferably at least one biasable lever with a hook. According to embodiments of the present disclosure the surface of the at least one second biasable member and/or the surface of the plunger rod which interact in order to inhibit movement of the plunger rod in the proximal direction when the plunger rod is in the locked position is tapered and/or angled such that, when the biasable member is able to recoil, the biasable member is deflected by the plunger rod being pushed in the proximal direction by the output axial force from the second energy accumulating member. Preferably, the at least one second biasable member is deflected in a radially outward direction, away from the longitudinal axis of the injection device.

According to embodiments of this disclosure the injection device further comprises a third energy accumulating member. The sleeve may be operationally associated with said third energy accumulating member such that the sleeve is axially moveable in relation to the housing towards the distal end of the injection device from a starting position to a retracted position against an axial force from said third energy accumulating member and/or such that the sleeve is axially moveable in relation to the housing a predetermined distance towards the proximal end of the injection device due to an output axial force from said third energy accumulating member from the retracted position to a final position.

The starting position of the sleeve may be the initial position of the sleeve, i.e., the position of the sleeve after the front cap has been removed from the device and before the device has been located at the delivery site. In this position, the sleeve may extend past the outer body or protrude from said outer body in a proximal direction of the device, e.g., when the front cap is removed. Alternatively or additionally, the needle cover may be operationally associated with said sleeve and extend out of or protrude from the outer body in a proximal direction of the device. The sleeve and/or the needle cover may cover the needle before penetration is performed.

The retracted position of the sleeve may be the position of the sleeve when the device is positioned at the delivery site and pushed against a patient's skin. When the sleeve or, alternatively, the needle cover protrudes from the proximal end of the outer body, the sleeve may be moved towards the distal end of the injection device from the starting position to the retracted position against the axial force from the third energy accumulating member by pushing the device against the delivery site. Incidentally, when the sleeve is moved towards the distal end of the injection device, the at least one first opening and/or the at least one first recess of the sleeve will overlap the at least one first biasable member, triggering penetration and injection as described above.

Following medicament injection, when the device is retracted from the delivery site, the sleeve may be axially moved in relation to the housing a predetermined distance towards the proximal end of the injection device due to an output axial force from the third energy accumulating member from the retracted position to the final position. When reaching the final position, movement of the sleeve relative to the housing towards the distal end of the injection device may be substantially inhibited by at least one third biasable member recoiling and interacting with the sleeve.

The at least one third biasable member may comprise at least one biasable lever. In embodiments, the at least one third biased member is formed integrally with the inner body and, more preferably, is formed integrally with a tubular portion of the inner body which is at least partially disposed between the plunger holder and the sleeve. The sleeve may, thus, be partially arranged around the inner body.

According to embodiments of the present disclosure, the plunger holder interacts with the sleeve to substantially inhibit movement of the sleeve towards the proximal end of the injection device from the starting position into the final position when the plunger holder is in the initial position. For example, the plunger holder may be provided with a stop structure that restricts the movement of the sleeve in the proximal direction of the device. In this case, the sleeve will be able to move further towards the proximal end of the injection device once the plunger holder has moved from the initial position to the position following needle penetration and, thus, the sleeve will only be able to reach its final position after needle penetration is performed. The needle, which protrudes from the outer body after needle penetration because the container holder has been moved towards the proximal end of the injection device, preferably is covered by the sleeve and/or the needle cover when the sleeve reaches the final position.

Preferably, the at least one third biasable member, e.g., the corresponding lever of the inner body, is in a relaxed state when the sleeve is in the starting position. For this purpose, the sleeve may be provided with at least one second opening and/or at least one second recess overlapping said third biasable member in the starting position and in the retracted position. The third biasable member may be arranged such that it is deflected when the sleeve is moved towards the proximal end of the injection device from the retracted position to the final position and subsequently recoils when being overlapped by at least one opening and/or at least one recess of the sleeve. The third biasable member may be arranged such that movement of the sleeve towards the distal end of the injection device is inhibited thereafter. For example, the third biasable member may have a tapered and/or angled configuration such that it can only be deflected by the sleeve when said sleeve moves towards the proximal end of the injection device.

The first energy accumulating member, the second energy accumulating member and the third energy accumulating member may be arranged in the interior of the housing of the injection device and may be adapted to accumulate and store energy. The first, second and third energy accumulating members may be spirally wound compression springs. In embodiments, the first energy accumulating member is fitted into the tubular portion of the inner body and disposed between the plunger holder and the inner body. The second energy accumulating member may be fitted into the plunger rod and compressed between a proximal bottom of the plunger rod and a distal end of the plunger holder. The third energy accumulating member may be fitted between the sleeve and the inner body.

The first and second energy accumulating members may be at least partially compressed in the initial position of the device.

According to the present disclosure the injection device may further comprise a spring guide rod. The spring guide rod may be positioned in the plunger rod and abut against the plunger holder in order to guide the second energy accumulating member. Furthermore, a sleeve guide may be provided. The sleeve guide may be fixedly supported by the inner body and/or integrally to the rear cap and may guide the movement of the sleeve when the sleeve is moved towards the distal end of the injection device.

In embodiments, the window may be configured to allow inspection of the medicament before use. Furthermore, the window may be configured to allow assessing whether the device has been used or not and/or to allow assessing whether a dose has been fully injected. For example, the window may give a clear view of the medicament container before use and a clear view of the plunger rod disposed within the medicament container thereafter. When arranged around the container holder, the sleeve and/or the needle cover may comprise openings in order to allow inspection of the medicament container.

BRIEF DESCRIPTION OF THE FIGURES

The following Figures below disclose an embodiment of the disclosure for illustrational purposes only. In particular, the disclosure within the Figures is not meant to limit the range of protection of the present disclosure. The embodiment shown may be modified in many ways within the scope of the claims.

FIG. 2 shows a first exploded view of the injection device according to the preferred embodiment of FIG. 1;

FIG. 3 shows a perspective view of a container holder and a medicament container of the injection device according to the preferred embodiment of FIG. 1;

FIG. 4 shows a perspective view of a sleeve of the injection device according to the preferred embodiment of FIG. 1;

FIG. 5 shows a perspective view of a plunger holder of the injection device according to the preferred embodiment of FIG. 1;

FIG. 6 shows a perspective view of an inner body of the injection device according to the preferred embodiment of FIG. 1;

FIG. 7 shows a perspective view of a needle cover the injection device according to the preferred embodiment of FIG. 1;

FIG. 8 shows a cross-sectional view of the injection device according to the preferred embodiment of FIG. 1, the sectional plane being perpendicular to the longitudinal axis of the device;

FIG. 9 shows a cross-sectional view of the injection device according to the preferred embodiment of FIG. 1 in the initial position, the sectional plane being parallel to the longitudinal axis of the device;

FIG. 10 shows a further cross-sectional view of the injection device according to the preferred embodiment of FIG. 1 in the initial position, the sectional plane being parallel to the longitudinal axis of the device;

FIG. 11 shows a detail of the cross-sectional view of FIG. 10;

DETAILED DESCRIPTION

Figure 1:
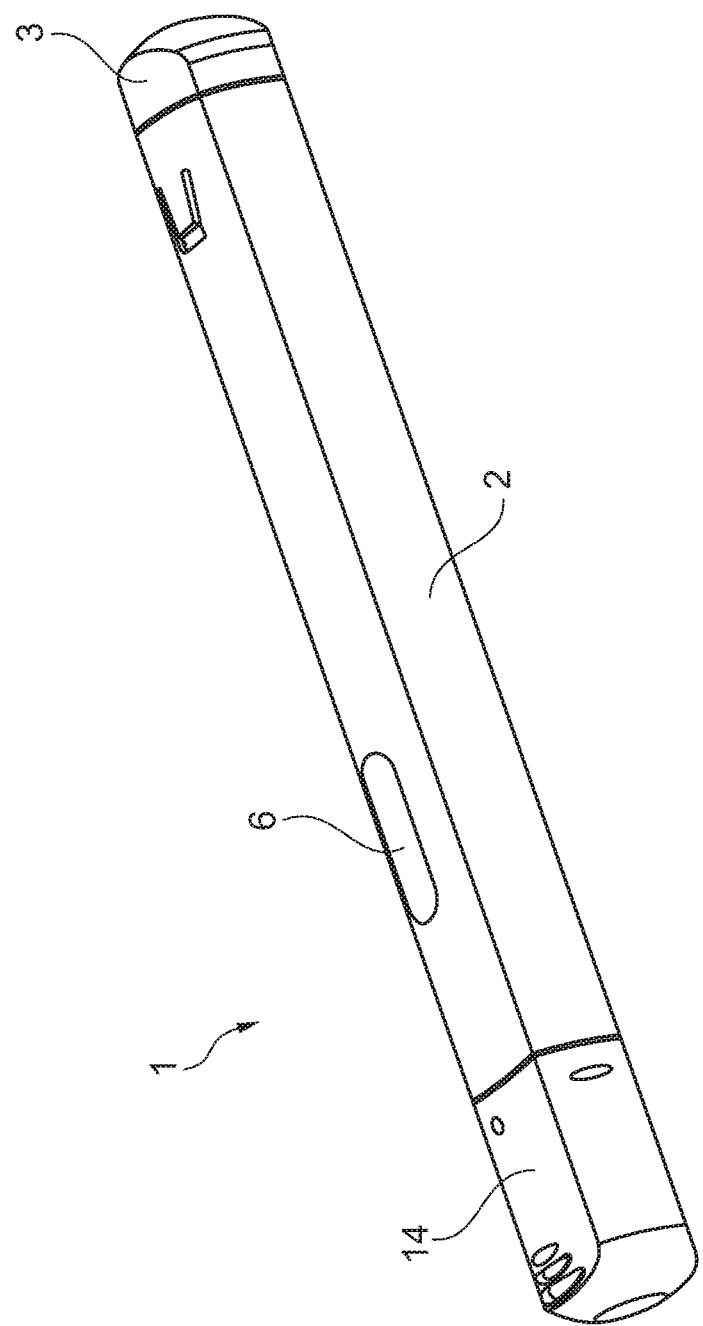
FIG. 1 shows a perspective view of an injection device according to a preferred embodiment of the present disclosure.

FIG. 1 shows a perspective view of an injection device according to a preferred embodiment of the present disclosure. The injection device 1 has a housing that comprises an outer body 2 and a rear cap 3.

As shown in FIG. 1, the outer body 2 comprises at least one window 6. Such a window allows the user to view the state of the injection, i.e. whether the injection device 1 is still in its initial position with the medicament not yet being injected, or whether the medicament container is already emptied. Through window 6, the user can see the medicament container accommodated inside the outer body 2.

Furthermore, FIG. 1 shows front cap 14 which closes the proximal opening of the outer body 2 until the injection device 1 is used.

Figure 13:
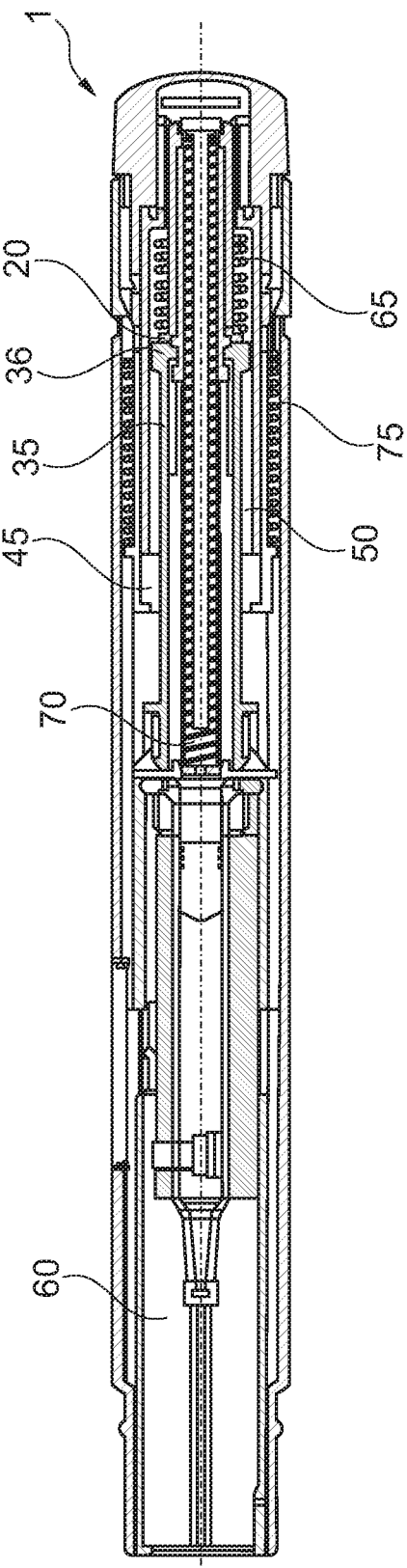
FIG. 13 shows a further cross-sectional view of the injection device according to the preferred embodiment of FIG. 1, the sectional plane being parallel to the longitudinal axis of the device and the sleeve being in the retracted position.

FIG. 2 shows a first exploded view of the injection device 1 according to the preferred embodiment of FIG. 1. In this exploded view of FIG. 2, the outer body 2, the rear cap 3, the window 6 as well as the front cap 14 are shown "removed" from the injection device 1. In the assembled state of the injection device, the rear cap may close the distal opening of the outer body. As shown in FIG. 2, the rear cap 3 may be provided with engagement structures such as circumferential groove-rib-structures for form-fitting the rear cap to the outer body. Further, as best visible in FIG. 13, the rear cap 3 comprises slots which are engaged by hooks of the inner body 50 in order to fixedly hold the rear cap 3 to the outer body 2. However, the rear cap may also comprise slots and/or hooks for being engaged directly to the outer body 2. Furthermore, the connection may be releasable. In this case the outer body 2 and the rear cap 3 can be easily disconnected so that the inner components of the device can be pulled out of the outer body 2 and a medicament container can be inserted into or removed from the injection device 1. Further between the rear cap 3 and the inner body is positioned a sleeve guide (not shown) that may be fixedly supported by the inner body and/or integrally to the rear cap.

As further shown in FIG. 2, the injection device according to the preferred embodiment of FIG. 1 also comprises a medicament container holder 10 arranged within the outer body 2. The container holder 10 is configured for accommodating a medicament container 11. As shown in FIG. 2 the medicament container 11 may be a commonly used medicament container having a needle 12 attached to one end thereof and a stopper 13 sealingly and slidable arranged inside said medicament container 11 at the other end thereof. However, according to other embodiments of the disclosure, the needle may also be attached to the container holder 10 and be fluidly connectable to a medicament container 11 when such a container is inserted into the container holder 10. Preferably, the medicament container contains a defined dose of a substance to be injected, such as a medicament, insulin or hormones.

In the fully assembled state of the injection device 1, the medicament container holder 10 is at least with its proximal end located within the outer body 2. This will be described in more detail below with reference to FIG. 9. In the preferred embodiment shown in FIG. 2, the medicament container holder 10 comprises at least one container holder guide 19.

As also shown in FIG. 2, the injection device according to the preferred embodiment of FIG. 1 further comprises a sleeve 45, which may be operationally associated with a third energy accumulating member 75 (third compression spring 75), and a plunger holder 35, which is operationally associated with a first energy accumulating member 65 (first compression spring 65). Furthermore, a plunger rod 20, operationally associated with a second energy accumulating member 70 (second compression spring 70) located therein, and an inner body 50 are provided. Although the first, second and third energy accumulating members preferably are spirally wound compression springs, also other structures capable of storing the required amount of energy may be provided within the scope of the present disclosure.

According to the preferred embodiment, the injection device also comprises a needle cover 60 located in the outer body 2. However, it should be noted that the needle cover 60 may be incorporated in sleeve 45, i.e., that needle cover 60 and sleeve 45 may be integrally formed and constitute a single element.

As best visible in FIG. 3, the container holder may further comprise a flexible collar 18. The flexible collar 18 is bend open when the medicament container 11 is inserted into the container holder 10 and snaps back subsequently, surrounding and holding the container 11.

FIG. 4 shows a perspective view of the sleeve 45 of the injection device 1 according to the preferred embodiment of FIG. 1. As shown, sleeve 45 may have the general shape of a hollow cylinder. However, any other suitable shape may be used and, for example, the sleeve may also have the shape of a hollow prism.

According to the preferred embodiment, the sleeve 45 has tongues 49 extending in the longitudinal direction thereof towards the distal end of the injection device at opposite sides of the sleeve. As further shown in FIG. 4, according to the preferred embodiment the sleeve 45 comprises a first pair of openings 46, which may be provided in tongues 49, a second pair of openings 47, and a third pair of openings 48. The openings of each of these pairs may be provided at opposite sides of the sleeve 45. As shown in FIGS. 1 and 4, the sleeve 45 may comprise a circumferential rib or other support structures for supporting the third energy accumulating member 75.

FIG. 5 shows a perspective view of the plunger holder 35 of the injection device 1 according to the preferred embodiment of FIG. 1. Also the plunger holder 35 is shown having the general shape of a hollow cylinder. However, also the plunger holder 35 may have any other suitable shape and, for example, may have the shape of a hollow prism.

As illustrated in FIG. 5, the plunger holder of the injection device 1 according to the preferred embodiment comprises second biasable members 36, which are provided as second levers 36. Preferably, the second levers 36 are integrally formed with the plunger holder 35. The plunger holder 35 is further provided with an inspection opening 37 which is aligned with the second pair of openings 47 for inspecting that the plunger rod is in place when assembling the device.

According to the preferred embodiment, the plunger holder 35 is arranged for being connectable to the container holder by a snap connection provided at the proximal end of the plunger holder 35 and featuring engageable hooks 38. Said hooks 38 may interact with slots, recesses or protrusions provided to the container holder 10. When the device is in the initial position, stop structure 39, which will be described in more detail with reference to FIG. 11 below, prevents the sleeve 45 from being pushed towards the proximal end of the injection device 1.

FIG. 6 shows a perspective view of the inner body 50. According to the preferred embodiment, two first biasable members are provided as first levers 51 (not shown in FIG. 6) and two third biasable members are provided as second levers 52, first levers 51 and second levers 52 being integrally formed with a tubular portion 53 of the inner body 50. Furthermore, inner body 50 comprises slots 54 for being snap fitted with the outer body 2 and hooks 55 for holding the rear cap 3.

FIG. 7 illustrates a perspective view of the needle cover 60 of the injection device 1 according to the preferred embodiment of FIG. 1. As shown, needle cover 60 may comprise protrusions 62 with slots for guiding the needle cover 60 along ribs provided in the outer body 2. As best visible in FIG. 8, the container holder 10 may comprise several container holder guides 19 that are arranged at opposite sides of the container holder, and extend in longitudinal direction thereof. According to the preferred embodiment the container holder guides 19 may be received in corresponding guide slots 61 provided at the inner surface of the needle cover 60.

FIG. 9 shows a cross-sectional view of the injection device according to the preferred embodiment of FIG. 1, the sectional plane being parallel to the longitudinal axis of the device. The device is shown in the initial position, i.e., as it may be delivered to the patient. The device is shown without the front cap 14.

As illustrated in FIG. 9, the container holder 10 preferably is located within the outer body 2 such that the needle 12 is covered by said outer body. The first compression spring 65 is compressed between plunger holder 35 and the inner body 50 such that the plunger holder is pushed towards the proximal end of the device 1. However, the hooks provided at the end of the first levers 51 interact with a notch provided in plunger holder 35 and thereby inhibit movement of the plunger holder 35 towards the proximal end of the device 1 along the longitudinal axis 16. As shown, e.g., in FIG. 9, the first levers 51 may be integrally formed with the inner body 50.

Similarly to FIG. 9, also FIG. 10 shows a cross-sectional view of the injection device according to the preferred embodiment of FIG. 1, the sectional plane being parallel to the longitudinal axis of the device. However, the position of the device is rotated by 90°.

According to the preferred embodiment the injection device 1 comprises a plunger rod 20 that is arranged such that a proximal end thereof contacts the stopper 13 of the medicament container 11. The plunger rod 20 is slidable with respect to the plunger holder 35 and slidable with respect to the container holder 10. Furthermore, the plunger rod 35 is operationally associated with the second compression spring 70 such that due to an output axial force from said second compression spring 70 the plunger rod 20 is axially moved in relation to the container holder 10 towards the proximal end of the injection device 1. The plunger holder 35 may be arranged around the plunger rod 20 and/or the plunger rod 20 may be arranged around the second compression spring 70.

When the device 1 is in the initial position, the second compression spring 70 preferably is compressed between a proximal bottom of the plunger rod 20 and a distal end of the plunger holder such that the plunger rod is pushed towards the proximal end of the device 1. However, according to the preferred embodiment shown in FIG. 10, the hooks provided at the end of the second levers 36 interact with a rib provided on the plunger rod 20 and thereby inhibit movement of the plunger rod 20 towards the proximal end of the device 1. Thus, the plunger rod 20 is in a locked position. It will be clear to the person skilled in the art that instead of a rib the plunger rod 20 may be provided with a recess.

The injection device 1 may comprise a spring guide rod 25 in order to guide the second compression spring 70.

As further illustrated in FIGS. 9 and 10, in the preferred embodiment the injection device 1 comprises the needle cover 60 which is attached to the sleeve 45. Furthermore, the device 1 comprises a third compression spring 75 which is operationally associated with the sleeve 45 and pushes the sleeve 45 and the needle cover 60 towards the proximal end of the device. As shown in the detail of FIG. 11, movement of the sleeve 45 and the needle cover 60 towards the proximal end of the injection device are restricted by the sleeve 45 abutting the stop structure 39 of the plunger holder 35. The needle cover 60 partially protrudes from the outer body 2 in the proximal direction of the device when the device 1 is in the initial position.

Figure 12:
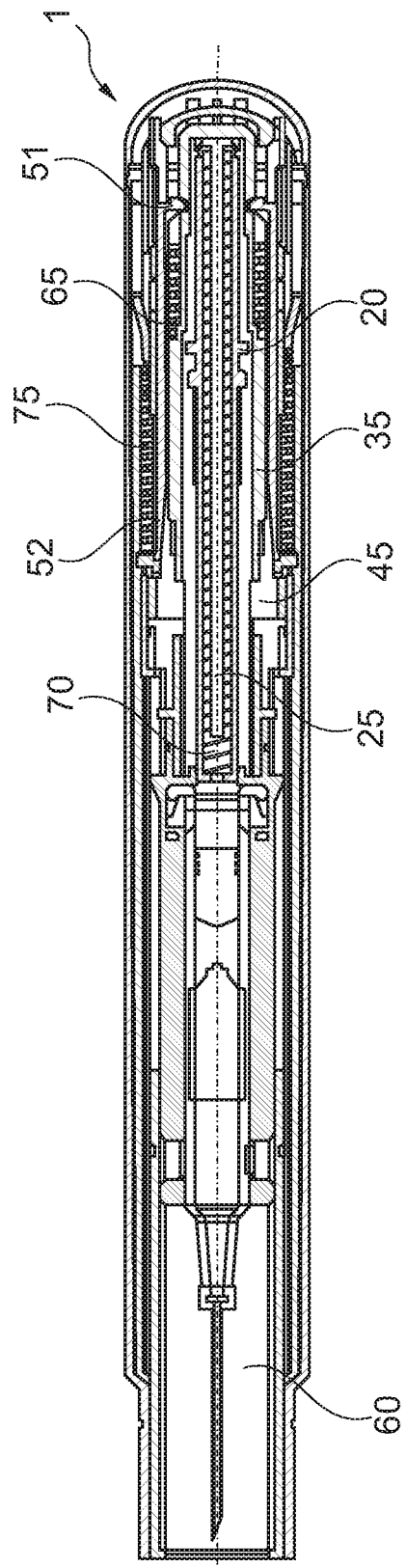
FIG. 12 shows a cross-sectional view of the injection device according to the preferred embodiment of FIG. 1, the sectional plane being parallel to the longitudinal axis of the device and the sleeve being in the retracted position.

In the initial position shown in FIGS. 9 and 10 the first levers 51 are overlapped by the sleeve 45 and, thus, are unable to be deflected and/or to recoil. FIG. 12, however, shows the device when located at an injection site and being pushed against the skin of a patient. In this case the sleeve 45 is axially moved in relation to the housing towards the distal end of the injection device 1 from the starting position to a retracted position against the axial force from the third compression spring 75. The sleeve is then in the retracted position and the first pair of openings 46 overlaps the first levers 51. Since the first levers 51 are able to recoil and/or can be deflected, the plunger holder 35 and the container holder 10 are moved towards the proximal end of the injection device 1 by the output force from the first compression spring 65. Thereby, penetration is performed.

Figure 14:
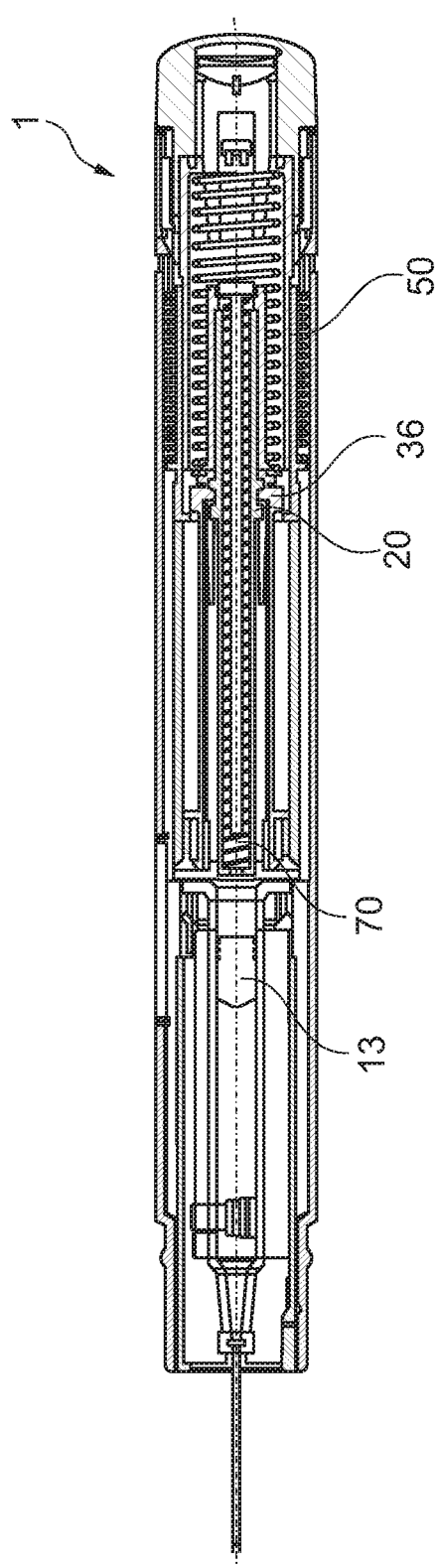
FIG. 14 shows a cross-sectional view of the injection device according to the preferred embodiment of FIG. 1 following needle penetration with the plunger rod being in the locked position, the sectional plane being parallel to the longitudinal axis of the device.

Thus, as illustrated in the sequence of FIGS. 13 to 16, second levers 36 continue to abut against the inner body 50 (see FIG. 13) until the needle 12 reaches the final penetration depth and the second levers 36 move past the proximal end of said inner body 50. Thus, the plunger rod 20 is maintained in the locked position until the final penetration depth is reached. As shown in FIG. 14, a flange of the container holder 10 may abut a step of the outer body 2 to restrict movement of the container holder 10 and the plunger holder 35 towards the proximal end of the device 1 when the final penetration depth is reached.

According to the preferred embodiment shown in FIG. 14, the second levers 36 move past the proximal end of the inner body 50 when the final penetration depth is reached. The second levers 36 are, therefore, able to recoil and/or to be deflected, releasing the plunger rod 20.

Figure 15:
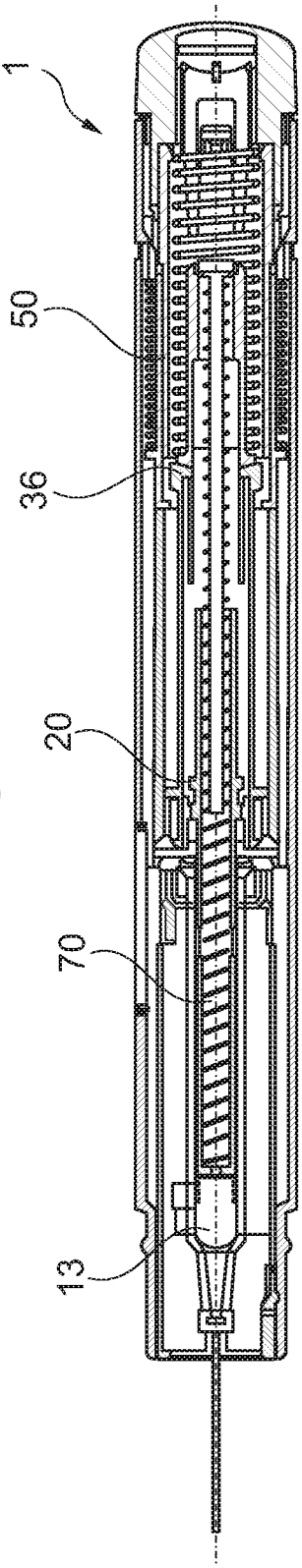
FIG. 15 shows a cross-sectional view of the injection device according to the preferred embodiment of FIG. 1 following medicament injection, the sectional plane being parallel to the longitudinal axis of the device.

As shown in FIG. 15 the plunger rod is then moved towards the proximal end of the injection device 1 by the output axial force of the second compression spring 70, thereby pushing the stopper 13 along the medicament container 11 and injecting the medicament.

Figure 16:
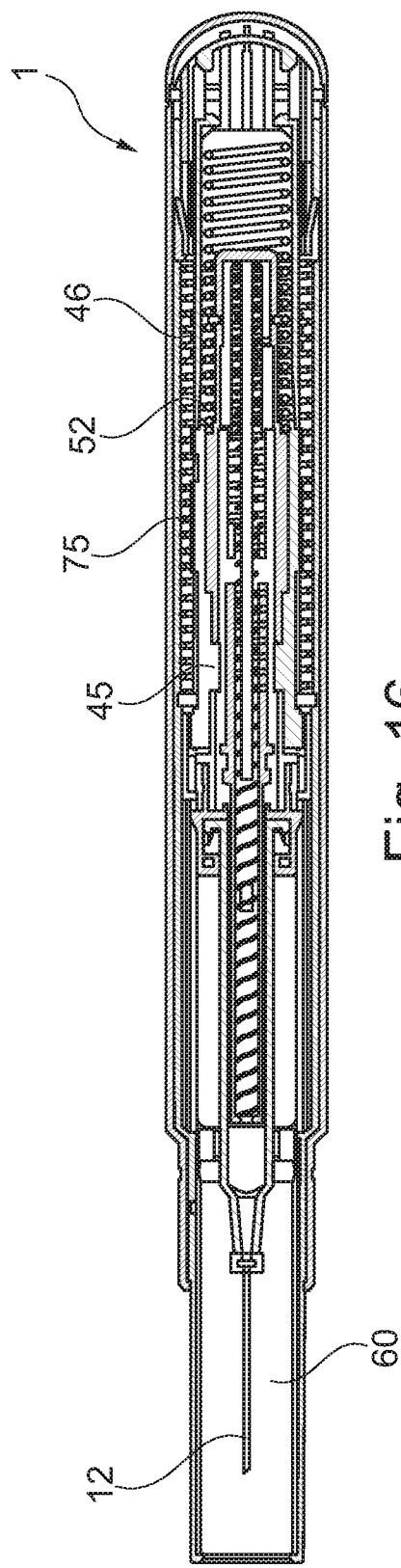
FIG. 16 shows a cross-sectional view of the injection device according to the preferred embodiment of FIG. 1 with the sleeve being in the final position, the sectional plane being parallel to the longitudinal axis of the device.

Following medicament injection, when the device 1 is retracted from the delivery site, the sleeve 45 is axially moved in relation to the housing a predetermined distance towards the proximal end of the injection device 1 due to the output axial force from the third compression spring 75 from the retracted position to a final position. As illustrated in FIG. 16, the sleeve 45 may now reach its final position given that the plunger holder 35 has been displaced in the proximal direction during needle penetration. Thus, the sleeve 45 can move further towards the proximal end of the injection device before reaching the stop structure 39. As further shown in FIG. 16, movement of the sleeve 45 relative to the housing towards the distal end of the injection device 1 is inhibited by third levers 52 recoiling and abutting against the first pair of openings 46 provided in the sleeve 45 once the sleeve reaches its final position.

Figure 17:
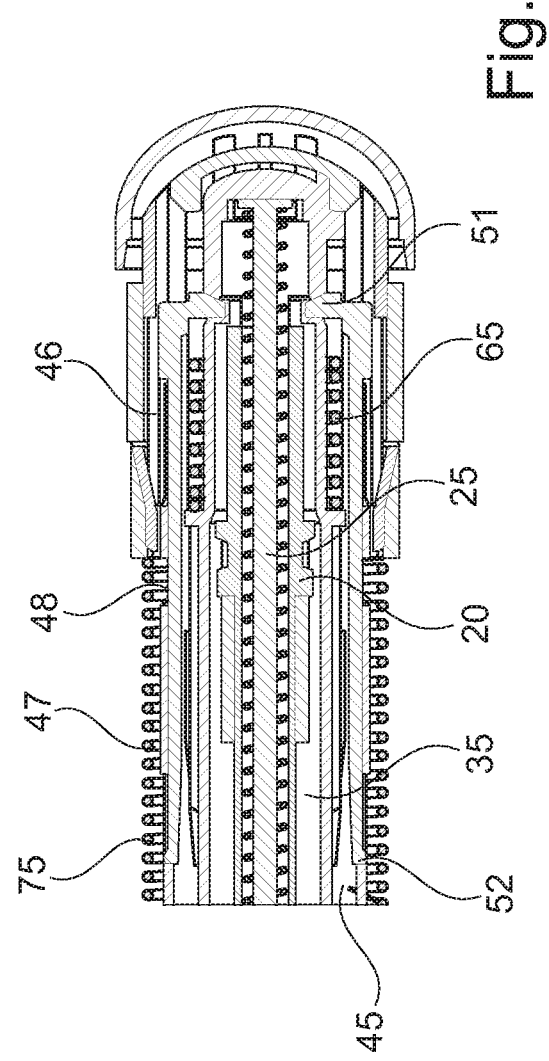
FIG. 17 shows a cross-sectional view of the distal part of the injection device according to the preferred embodiment of FIG. 1 in the initial position, the sectional plane being parallel to the longitudinal axis of the device.

As best visible in FIG. 17, the surface of the first levers 51 and/or the surface of the plunger holder 35 which abut in order to inhibit movement of the plunger holder in the proximal direction when the plunger holder is in the initial position is tapered according to the preferred embodiment. Therefore, when the first levers 51 are overlapped by the first opening 46 of the sleeve and are able to recoil, the levers 51 are deflected by the plunger holder 35, the latter being pushed in the proximal direction by the output axial force from the first compression spring 65. As shown in FIG. 17, the surfaces may be tapered such that the levers 51 are deflected away from the longitudinal axis of the injection device. However, the levers may also be biased when assembling the device and in this case tapered surfaces might not be required. Similarly, the surface of the second levers 36 and/or the surface of the plunger rod 20 which abut in order to inhibit movement of the plunger holder in the proximal direction until penetration is performed may also be tapered.

As will be recognized by those skilled in the art, the present disclosure provides an injection device requiring few parts to provide reliable, exact and safe medicament injection. Moreover, the device is comparatively easy to manufacture and can be assembled by successively sliding the components of the device over each other. Therefore, several disadvantages of the prior art are overcome.

While the present disclosure has been illustrated and described in detail in the drawings and the foregoing description, such illustration and description are to be considered illustrative or exemplary and not restrictive. It should be noted that the disclosure covers all further features shown in the figures individually although they may not have been described in the afore description and it will be understood that changes and modifications may be made by those of ordinary skill within the scope of the following claims. In particular, the present disclosure covers further embodiments with any combination of features from different embodiments described above and below.

Furthermore, in the claims the word "comprising" does not exclude other elements or steps, and the terms "a", "an" "first", "second" etc. do not exclude a plurality. A single unit may fulfil the functions of several features recited in the claims. The terms "essentially", "about", "approximately" and the like in connection with an attribute or a value particularly also define exactly the attribute or exactly the value, respectively. Any reference signs in the claims should not be construed as limiting the scope.

The invention claimed is:

1. A medicament delivery device comprising
   a housing for accommodation of a medicament container arranged with a needle, where the medicament container is moveable inside the housing between an initial position where the needle is arranged inside the housing, and a final position where the needle protrudes outside the housing;
   a plunger rod configured to be moved in the medicament container for delivering at least one dose of medicament;
   a plunger holder having at least one locking member configured to interact with a plunger rod stop to normally lock the plunger rod to the plunger holder;
   a first energy accumulating member configured to apply a force to the medicament container thereby moving the medicament container from the initial position to the final position, the first energy accumulating member being further configured to advance the plunger holder with the plunger rod to the final position;
   a second energy accumulating member comprising a plunger rod spring configured to apply a force to the plunger rod to advance the plunger rod in the medicament container for delivering at least one dose of medicament, where one end of the plunger rod spring is fixedly connected to the plunger holder,
   wherein the housing is configured to unlock the locking member and release the plunger rod from the plunger holder when the medicament container and the plunger holder is advanced to the final position, thereby activating the second energy accumulating member to advance the plunger rod in the medicament container for delivering of at least one dose of medicament;
   wherein the locking member comprises at least one deflectable member and wherein the housing is configured to allow for the at least one deflectable member to enable deflection away from the plunger rod when the medicament container and the plunger holder is advanced to the final position.

2. The medicament delivery device according to claim 1, wherein the plunger holder and the medicament container are interconnected so that the plunger holder cannot move in a longitudinal direction with respect to the medicament container, wherein the housing has a space arranged to receive said at least one deflectable member when the plunger holder is advanced to the final position.

3. The medicament delivery device according to claim 2, wherein the at least one deflectable member is configured to deflect upon entering the space of the housing.

4. The medicament delivery device according to claim 1, wherein the second energy accumulating member applies the driving force directly onto the plunger rod.

5. The medicament delivery device according to claim 1, wherein the housing further accommodates a container holder for holding the medicament container, and wherein the medicament container further comprises a flange is locked between the container holder and the plunger holder.

6. The medicament delivery device according to claim 1, wherein second energy accumulating member is provided inside the plunger holder and wherein the first energy accumulating member is provided outside the plunger holder.

7. The medicament delivery device according to claim 1, the device further comprising a third energy accumulating member, a sleeve being slidable arranged in relation to the housing and being operationally associated with said third energy accumulating member such that the sleeve is axially moveable in relation to the housing towards the distal end of the injection device from a starting position to a retracted position against an axial force from said third energy accumulating member such that due to an output axial force from said third energy accumulating member the sleeve is axially moveable in relation to the housing a predetermined distance towards the proximal end of the injection device from a retracted position to a final position.

8. The medicament delivery device according to claim 7, wherein, when the sleeve reaches a final position, movement of the sleeve relative to the housing towards the distal end of the injection device is substantially inhibited by at least one third biasable member recoiling and interacting with the sleeve.

9. The medicament delivery device according to claim 7, wherein, in the initial position of the plunger holder, movement of the sleeve towards the proximal end of the injection device from a starting position into a final position is substantially inhibited by the plunger holder interacting with the sleeve.

10. The medicament delivery device according to claim 7, wherein, in the starting position or in the final position, the needle is covered by a needle cover that is operationally associated with the sleeve.

11. The medicament delivery device according to claim 1, wherein the housing further comprises an inner body being substantially fixedly arranged in relation to the housing.

12. The medicament delivery device according to claim 11, comprising at least one first biasable member is formed integrally with the inner body, wherein, in the initial position of the plunger holder movement of the plunger holder towards the proximal end of the injection device is substantially inhibited by at least one first biasable member interacting with the plunger holder, the first biasable member recoiling when being overlapped by an opening or recess in the sleeve such that the plunger holder is released.

13. The medicament delivery device according to claim 12, wherein the at least one first biasable member is formed integrally with a tubular portion of the inner body at least partially disposed between the plunger holder and the sleeve.

14. The medicament delivery device according to claim 11 further comprising at least one third biasable member is formed integrally with the inner body, wherein, when the sleeve reaches a final position, movement of the sleeve relative to the housing towards the distal end of the injection device is substantially inhibited by at least one third biasable member recoiling and interacting with the sleeve.

15. A medicament delivery device comprising
a housing comprising a first lever;
a container holder;
a needle cover having a distal end connected to a sleeve, the sleeve having an opening at a distal end;
a plunger rod positioned within a plunger holder, where the plunger holder comprises a second lever locked to the plunger rod when the plunger holder is in an initial position such that the plunger rod is prevented from axial movement relative to the container holder; and
a plunger rod spring positioned within the plunger rod that exerts a biasing force on the plunger rod in the proximal direction, where one end of the plunger rod spring is fixedly connected to the plunger holder,
wherein proximal movement of the plunger holder relative to the housing causes the second lever to recoil radially outward and unlocking the plunger rod and causing the plunger rod spring to move the plunger rod proximally relative to the housing and the plunger holder.

16. The medicament delivery device of claim 15 where the first lever is engaged with the plunger holder to prevent the plunger holder from proximal movement relative to the housing.

17. The medicament delivery device of claim 16 wherein distal movement of the needle cover and the sleeve relative to the housing causes the opening to move adjacent the first lever and allows the first lever to recoil radially outward into the opening disengaging from the plunger holder, where the plunger holder moves proximally under a biasing force of energy accumulating member.

18. The medicament delivery device of claim 15 where the housing further comprises a third lever that engages the sleeve when the needle cover moves to a final position to prevent axial movement of the needle cover in the distal direction.

* * * * *